US011295845B2

(12) United States Patent
Kelly et al.

(10) Patent No.: US 11,295,845 B2
(45) Date of Patent: Apr. 5, 2022

(54) INFUSION PUMP LINE CONFIRMATION

(71) Applicant: CERNER INNOVATION, INC., Kansas City, KS (US)

(72) Inventors: Lisa Kelly, Overland Park, KS (US); Bryan Muehlmeier, Overland Park, KS (US); Gregory Locker, Kansas City, MO (US)

(73) Assignee: CERNER INNOVATION, INC., North Kansas City, MO (US)

( * ) Notice: Subject to any disclaimer, the term of this patent is extended or adjusted under 35 U.S.C. 154(b) by 1247 days.

(21) Appl. No.: 14/965,461

(22) Filed: Dec. 10, 2015

(65) Prior Publication Data

US 2017/0165413 A1  Jun. 15, 2017

(51) Int. Cl.
  *G16H 20/17*  (2018.01)
  *A61M 5/142*  (2006.01)
  *G16H 40/63*  (2018.01)
  *G16H 10/60*  (2018.01)
  *A61M 5/14*  (2006.01)

(52) U.S. Cl.
  CPC .......... *G16H 20/17* (2018.01); *A61M 5/142* (2013.01); *G16H 10/60* (2018.01); *G16H 40/63* (2018.01); *A61M 5/14* (2013.01); *A61M 2005/14208* (2013.01); *A61M 2205/3584* (2013.01); *A61M 2205/502* (2013.01); *A61M 2205/52* (2013.01); *A61M 2205/6009* (2013.01); *A61M 2205/6054* (2013.01)

(58) Field of Classification Search
  None
  See application file for complete search history.

(56) References Cited

U.S. PATENT DOCUMENTS

| 2004/0167465 A1 | 8/2004 | Mihai et al. |
| 2007/0233521 A1* | 10/2007 | Wehba .......... A61M 5/142 705/3 |
| 2009/0270833 A1* | 10/2009 | DeBelser ......... G06Q 10/10 604/500 |

(Continued)

FOREIGN PATENT DOCUMENTS

JP    3688994 B2 *  8/2005  ............ A61M 16/01

OTHER PUBLICATIONS

Shi, H. (2015). Context awareness via a smartphone based active RFID proximity detection system (Order No. 1594958). Available from ProQuest Dissertations and Theses Professional. (1710075367). Retrieved from https://dialog.proquest.com/professional/docview/1710075367?accountid=131444 (Year: 2015).*

(Continued)

*Primary Examiner* — Lena Najarian
(74) *Attorney, Agent, or Firm* — Shook, Hardy & Bacon LLP

(57) ABSTRACT

Methods, computer systems and computer readable media cause an infusion pump to provide visual confirmation of line checks. In embodiments, an indication is provided that one or more infusions need a line check. A selection of on the one or more infusion is received. Information corresponding to the selection of the one of the one or more infusions is received from an electronic medical record (EMR) and communicated to a corresponding infusion pump. The infusion pump then provides a visual indication of the line check.

19 Claims, 7 Drawing Sheets

(56) References Cited

U.S. PATENT DOCUMENTS

| | | |
|---|---|---|
| 2009/0299770 A1 | 12/2009 | Martinez et al. |
| 2010/0169120 A1 | 7/2010 | Herbst et al. |
| 2012/0042366 A1* | 2/2012 | Jin .......................... G06F 21/35 |
| | | 726/7 |
| 2014/0194817 A1 | 7/2014 | Lee et al. |
| 2014/0288947 A1* | 9/2014 | Simpson ............. A61M 5/1723 |
| | | 705/2 |
| 2016/0051750 A1 | 2/2016 | Tsoukalis |

OTHER PUBLICATIONS

Final Office Action received for U.S. Appl. No. 14/965,454, dated Jul. 10, 2019, 17 pages.
Preinterview First Office Action received for U.S. Appl. No. 14/965,454, dated Nov. 16, 2018, 4 pages.

* cited by examiner

INFUSION PUMP LINE CONFIRMATION

BACKGROUND

Infusion pumps infuse fluids, medications and/or nutrients into the circulatory system of an individual or patient. The infusions may be intravenous, arterial, epidural and the like. Infusion pumps can administer injections continuously, intermittently, or upon patient request. Infusion pumps are used by clinicians for patients when more accuracy is needed than with manually adjusted gravitational administration of fluids into a patient's circulatory system. Infusions pumps can be used for infusion of a variety of fluids and medications including, but not limited to anesthesia, chemotherapy, IV drugs, blood transfusions and the like.

In a typical workflow, a clinician must follow a particular order before certain medical devices that are used to treat or care for a patient, such as infusion pumps, can begin treating a patient. When the particular order is not followed, the devices enter an error state that causes the clinician to have to reset the device and start the process over. This is typically a manual process that involves the use of a barcode scanner. The clinician must scan each of the barcodes associated with the patient, the infusion, and the device before the patient is able to be treated. Additional delays may result if the clinician does not follow the appropriate order or if communication between the pump and an infusion application (or healthcare information system) is not yet established. In cases where the patient is receiving multiple infusions from multiple pumps, the clinician may be required to confirm the right pump is programmed with the right order at the right sight. However, with several infusion lines present, it is often difficult and time consuming to confirm the correct pump. Each of these delays can affect timeliness and effectiveness of patient care and may also frustrate the clinician, the patient, and family members of the patient.

SUMMARY

Embodiments of the present invention generally relate to causing an infusion pump to provide visual confirmation of line checks. In this way, an indication is provided that one or more infusions need a line check. A selection of on the one or more infusion is received. Information corresponding to the selection of the one of the one or more infusions is received from an EMR and communicated to a corresponding infusion pump. The infusion pump then provides a visual indication of the line check.

Accordingly, in one aspect, an embodiment of the present invention is directed to one or more computer storage media storing computer-useable instructions that, when used by one or more computing devices, cause the one or more computing devices to perform operations. The operations include providing, via a user interface on a clinician device, one or more infusions that need a line check. The operations also include receiving a selection, via an interaction with the user interface on the clinician device, one of the one or more infusions. The operations further include providing, via the user interface on the clinician device, an indication of the selection. The operations also include communicating a line check message to an infusion pump corresponding to the selection.

In another embodiment, an aspect is directed to a computer-implemented method in a clinical computing environment. The method includes providing a user interface indicating that one or more infusions need a line check. The method also includes receiving a selection of one of the one or more infusions. The method further includes receiving information corresponding to the selection of the one of the one or more infusions from an EMR. The method also includes communicating the information corresponding to the selection of the one of the one or more infusions to a corresponding infusion pump. The method further includes causing the infusion pump to provide a visual indication of the line check. Each computing process is performed by one or more computing devices.

A further embodiment is directed to a system comprising: one or more processors; and one or more computer storage media storing instructions that, when used by the one or more processors, cause the one or more processors to: provide an indication that one or more infusions need a line check; receive a selection of one of the one or more infusions; receive information corresponding to the selection of the one of the one or more infusions from an EMR; communicate the information corresponding to the selection of the one of the one or more infusions to a corresponding infusion pump; and cause the infusion pump to provide a visual indication of the line check.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

As mentioned above, a clinician typically must follow a very particular order in a workflow before certain medical devices that are used to treat or care for a patient, such as infusion pumps, can begin treating a patient. If the particular order is not followed, an error is received that requires the clinician to have to reset the device and start the process over. For example, in the case of an infusion pump, a typical workflow includes: 1) scan the patient's wristband; 2) scan the medication; 3) scan the infusion pump; 4) review and confirm infusion characteristics on the infusion pump; 5) sign the order. When a particular order is not followed, the devices enter an error state that causes the clinician to have to reset the device and start the process over. In cases where the patient is receiving multiple infusions from multiple pumps, the clinician may be required to confirm the right pump is programmed with the right order at the right sight (i.e., a line check). However, with several infusion lines present, it is often difficult and time consuming to confirm the correct pump. Each of these delays can affect timeliness and effectiveness of patient care and may also frustrate the clinician, the patient, and family members of the patient.

Embodiments of the present invention generally relate to causing an infusion pump to provide visual confirmation of line checks. In this way, an indication is provided that one or more infusions need a line check. A selection of on the one or more infusion is received. Information corresponding to the selection of the one of the one or more infusions is received from an EMR and communicated to a corresponding infusion pump. The infusion pump then provides a visual indication of the line check.

Figure 1:
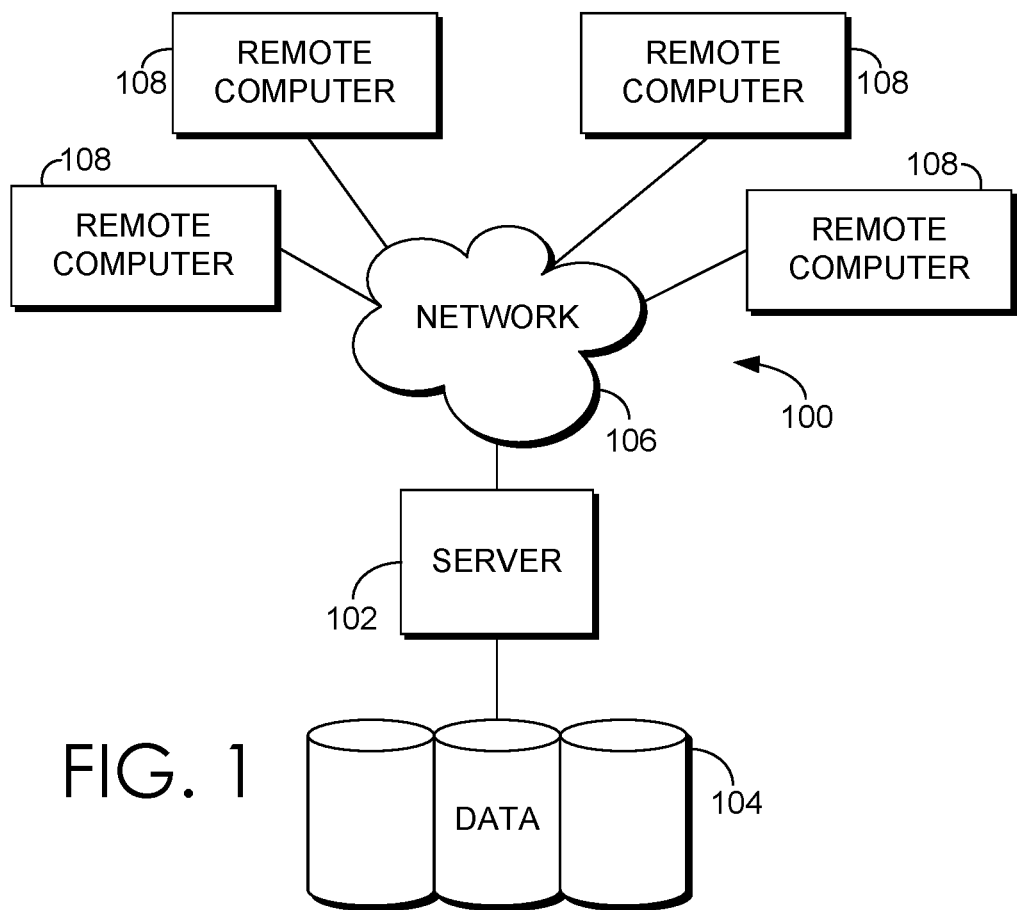
FIG. 1 is a block diagram of an exemplary computing environment suitable to implement embodiments of the present invention.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and non-volatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 104, provide storage of computer readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, students, office assistants and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Figure 2:
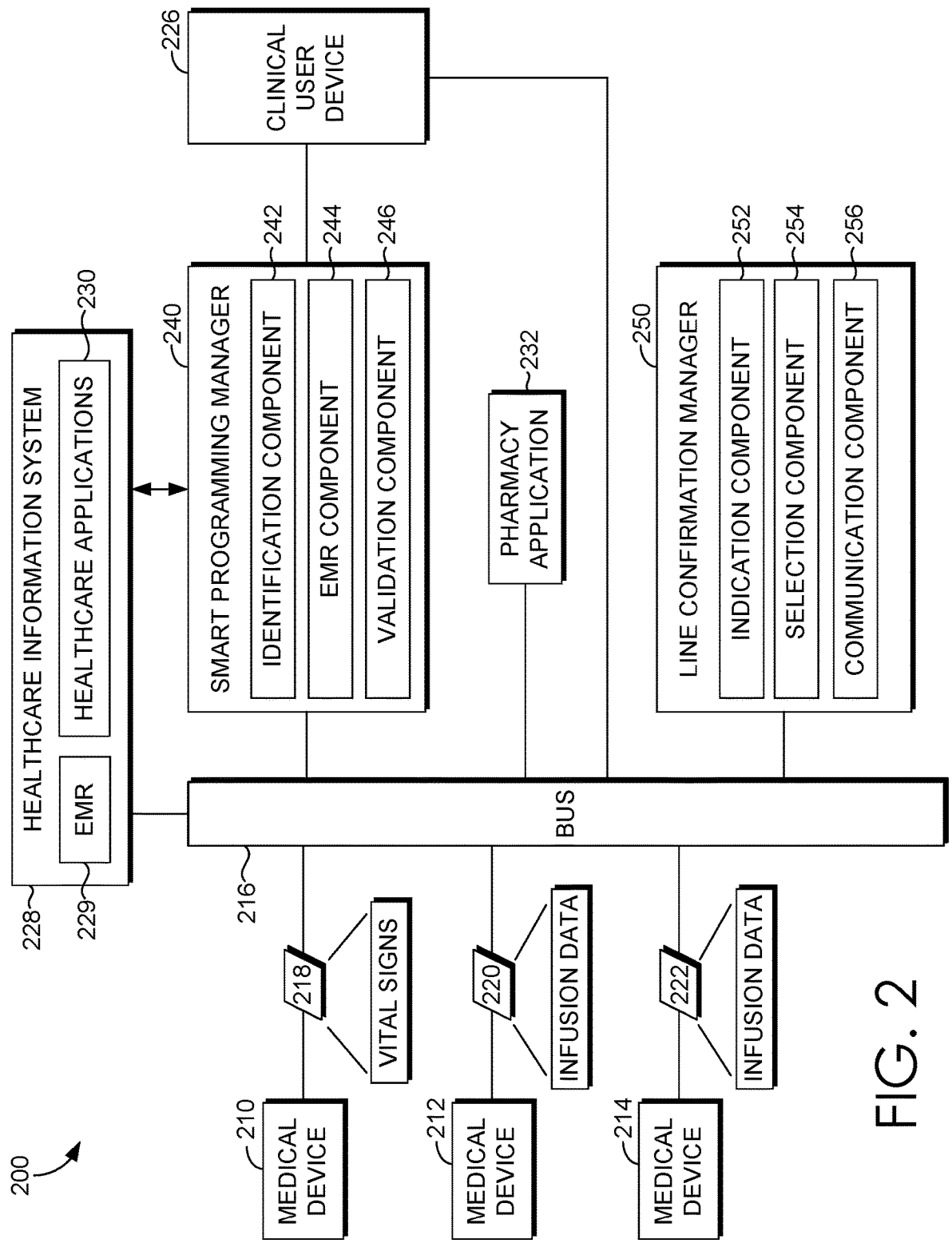
FIG. 2 is an exemplary system architecture suitable to implement embodiments of the present invention.

Turning now to FIG. 2, a schematic diagram depicts an operating environment, identified generally by reference numeral 200, suitable to practice an embodiment of the present invention. FIG. 2 includes various components that communicate with one another, including medical device 210, 212, 214, clinical user devices 226, bus 216, smart programming manager 240, line confirmation manager 250, healthcare information system 228 and pharmacy application 232. In one embodiment of the present invention, clinical user device 226 is a mobile or handheld device. The mobile or handheld device may be equipped with proximity and/or location based detection capabilities (e.g., Bluetooth or Radio-frequency identification (RFID)). Before describing in more detail how these components communicate, each component will be generally described.

In an embodiment of the present invention, medical device 210 might include cardiac monitors, ventilators, balloon pumps, patient beds, sequential-compression devices, electronic security devices, and vital-sign detecting devices. Medical device 210 may generate various data (e.g., measured heart rate) that, as described in more detail below, is communicated to other components (e.g., bus 216) of operating environment 200. Moreover, medical device 210 might also receive information from components of operating environment 200.

In another embodiment of the present invention, medical devices 212, 214 might include infusion pumps. Infusion pumps may infuse fluids, medications and/or nutrients into the circulatory system of an individual or patient. The infusions may be, but are not limited to, intravenous, arterial, epidural and the like. Infusion pumps can administer injections continuously, intermittently, or upon patient request. Infusion pumps are used by clinicians for patients when more accuracy is needed than with manually adjusted gravitational administration of fluids into a patient's circulatory system. Infusions pumps can be used for infusion of a variety of fluids and medications including, but not limited to anesthesia, chemotherapy, IV drugs, blood transfusions and the like. The fluid, medication and/or nutrients are typically contained in an infusion container, such as an infusion bag. It will be appreciate that any type container may be utilized to hold the infusion fluid, medication and/or nutrients. Infusion pumps 212 and 214 generate various data, including, but not limited to, remaining volume of infusion (e.g., amount remaining in fluid container), rate of infusion (e.g., how fast fluid is being infused), alerts (e.g., air in line, maintenance of pump needed, high backpressure, low infusion, occlusion, or pump stopped). This data is communicated to other components (e.g., bus 216) of operating environment 200. Moreover, infusion pumps 212 and 214 might also receive information from components of operating environment 200.

Healthcare information system 228 includes an integrated system of healthcare-related information that is usable by a healthcare facility to operate and provide patient care. For example, healthcare information system 228 includes an EMR and a healthcare applications component 230. EMR 229 includes an electronic version of patient records including information for the patient, such as medication and infusion orders, tasks, images, examination reports, testing and lab results, medical history, etc. Healthcare applications component 230 includes information that is input and provided at a patient's point-of-care (e.g., patient bedside) to assist healthcare professionals to provide appropriate care. An exemplary applications component 230 includes a patient order entry component for entering electronic healthcare orders for a patient. In an embodiment of the present invention, healthcare information system 228 receives information from other components, as will be described in more detail below. Moreover, healthcare information system 228 might also provide information that is communicated to other components of operating environment 200.

Clinical user devices 226 include devices that are used within a healthcare facility to receive, display, and send information. Exemplary clinical user devices 226 include any device capable of receiving, displaying, and sending information. In some embodiments, clinical user devices 226 receive information from other components of operating environment 200 based on location or proximity. In this way, clinical user devices 226 may receive information associated with a patient's wristband, a medication, or a medical device by being in the same location or in close proximity (e.g., Bluetooth or RFID range) and may not require physically scanning a barcode. Moreover, clinical user devices 226 might also receive inputs from a clinician that are communicated to other components of operating environment 200. Clinical user devices 226 also communicate to other components of operating environment 200 requests to receive additional information. For example, clinical user device 226 might communicate information to smart programming manager 240, line confirmation manager 250, pharmacy application 232, HIS 228, EMR 229, healthcare application 230, and medical devices 210, 212 and 214.

Pharmacy application 232 is an electronic application for receiving medication orders, such as infusion orders, to be filled. An exemplary pharmacy system is Cerner Millennium Pharmnet by Cerner Corporation, Kansas City Mo. Typically orders for medications, fluids and nutrients to be filled by a pharmacist are displayed in the pharmacy or pharmacy IV room. The pharmacist can use this information to drive the pharmacy workflow and make sure the necessary medication orders are filled. In another embodiment, infusion application 232 may be an automated pharmacy dispensing system such as Cerner RXStation by Cerner Corporation of Kansas City, Mo. The automated pharmacy system may be an apparatus pre-loaded with medication, fluids and/or nutrients that may be dispensed to fill patient orders.

As previously indicated, and as depicted in FIG. 2, each of medical devices 210, 212, 214, healthcare information system 228, smart programming manager 240, line confirmation manager 250, clinical user devices 226 and infusion application 232 may be in communication with bus 216. Bus 216 generally provides a connection framework for these components by creating and managing all connections, providing a messaging architecture to facilitate an exchange of information between the various components of FIG. 2, and providing general operational and management capabilities for connected devices. In one embodiment, medical devices 210, 212, 214, smart programming manager 240, line confirmation manager 250, clinical user devices 226, healthcare information system 228 and infusion application 232 communicate with bus 216 as described in U.S. patent application Ser. No. 12/347,475 (U.S. patent application Ser. No. '475), which is incorporated herein by reference. For example, medical devices 212, 214 might include various different types of infusion pumps that are manufactured by various different vendors. As such, components of FIG. 2 might communicate with bus 216 via a gateway (e.g., device gateway or internal gateway), an adapter, or by any other means described by U.S. patent application Ser. No. '475. In a further embodiment, bus 216 includes those capabilities described in U.S. patent application Ser. No. '475. As indicated in U.S. patent application Ser. No. '475, once data is received (e.g., data 218, 220, and 222) it can be sorted and routed to other applications.

In an embodiment of the present invention, such applications are included in smart programming manager 240 or line confirmation manager 250. As such, bus 216 might receive information (e.g., data 218, 220, and 222) and route the data to smart programming manager 240 and/or line confirmation manager 250. Moreover, bus 216 might receive information from pharmacy application 232 and route the information to smart programming manager 240 and/or line confirmation manager 250. In a further embodiment, bus 216 receives information from healthcare information system 228 and routes the information to smart programming manager 240 and/or line confirmation manager 250. In another embodiment, bus 216 receives information from smart programming manager 240 and/or line confirmation manager 250 and routes the information to other components. For example, bus 216 routes information from smart programming manager 240 and/or line confirmation manager 250 to medical device 210, 212, 214.

In an embodiment of the present invention, smart programming manager 240 communicates with bus 216 and functions to facilitate smart programming based on information received wirelessly and without requiring a clinician to scan barcodes. In this way, a clinician is only required to enter the room of a particular patient and the system automatically logs the clinician into the EMR with the appropriate context for a patient (e.g., infusion orders based on any infusions the clinician entered the room with and any infusion devices in the room). Information associated with the infusion is communicated to the appropriate components and the start of the infusion can be communicated to the EMR at the appropriate time.

Smart programming manager 240 includes identification component 242, EMR component 244, and validation component 246. While these components are included in the embodiment of FIG. 2, any number of components, either more or less than the illustrated components, may be used to accomplish the purposes of the present invention. Other components and subcomponents are contemplated to be within the scope of the present invention. Furthermore, although depicted as residing on one device, such as a server, it will be appreciated that any number of components and/or subcomponents may reside on any number of computing devices or servers. For example, one or more components of smart programming manager 240 may reside on medical devices 212, 214 and/or clinical user device 226.

Identification component 242 is generally configured to receive an identification of a patient associated with an order for an infusion. In this regard, the clinical user device 226 and the patient's wristband (or other identifier associated with the patient) may be equipped with Bluetooth capabilities. A Bluetooth connection may be established between the clinical user device 226 and the patient's wristband so the clinical user device 226 is able to receive an identification of the patient, such as when the clinician enters the same room as the patient. In another embodiment, the clinical user device 226 and the patient's wristband (or other identifier associated with the patient) may be equipped with other wireless capabilities. In this example, a wireless connection may be established between the clinical user device 226 and the patient's wristband so the clinical user device 226 is able to receive an identification of the patient. In another embodiment, the patient's wristband (or other identifier associated with the patient) may be equipped with a radio-frequency identification (RFID) tag. In this example, the clinical user device 226 may have an RFID reader so that it can read the patient's identification when the clinical user device 226 is near the patient's wristband that is equipped with the RFID tag.

Identification component 242 is also configured to receive an identification of the infusion or medication being administered to the patient by a medical device 210, 212, 214. As described above, clinical user device 226 may be equipped with Bluetooth (or other wireless capabilities). Likewise, the infusion or medication (or other identifier associated with the infusion or medication) may be also be equipped with Bluetooth or other wireless capabilities. A Bluetooth or wireless connection may be established between the clinical user device 226 and the infusion or medication so the clinical user device 226 is able to receive an identification of the infusion or medication. In some embodiments, the infusion or medication (or other identifier associated with the infusion or medication) may be equipped with a radio-frequency identification (RFID) tag. In this example, an RFID reader of the clinical user device 226 may be able to read the identification of the infusion or medication when the clinical user device 226 is near the infusion or medication that is equipped with the RFID tag.

In each of the Bluetooth, wireless, and RFID examples described above, the clinician may not actually have to scan the patient's wristband or the infusion or medication. Rather, the proximity of the clinical user device 226 (by virtue of the clinician's location) to the patient (by virtue of the patient's wristband or other identifier) and/or infusion or medication identifies each of the patient and/or infusion or medication, respectively. As can also be appreciated, other location tracking and/or proximity detection mechanisms commonly used in healthcare settings may also be utilized by identification component to identify the patient and/or the infusion or medication.

EMR component 244 is generally configured to automatically log the clinician into the EMR associated with the patient. Additionally, context, based on the clinician entering the room with the one or more infusions may automatically be provided. In this way, infusion information may automatically be populated and presented to the clinician via the EMR. Workflows associated with the infusions may also be provided to help guide the clinician through the step of preparing and starting the infusion.

Validation component 246 is generally configured to automatically validate the one or more infusions for the patient when the clinician enters the room. In this way, all associations between the patient, the room, the one or more infusions, the infusion pump, and the clinician are based on proximity and no scanning is required. This enables the workflow for all available infusions to be automatically provided to the clinician via a clinician device. Based on selections made by the clinician, and actions performed (e.g., hanging the infusion and turning on the pump), the clinician can select and confirm infusions, complete any necessary fields, and start the pump. The actual start of the infusion can then be communicated to the EMR and the pump is associated to the infusion. Once the nurse validates and signs the infusion in the EMR, via the validation component 340, infusion data can be documented.

In an embodiment of the present invention, line confirmation manager 250 communicates with bus 216 and functions to facilitate line confirmation of one or more infusions. In this way, a visual indication can be provided to the clinician to confirm a line for the appropriate pump at the appropriate time. Once the appropriate pump is confirmed the visual indication may be turned off and the process continues until all lines have been confirmed.

Line confirmation manager 250 includes indication component 252, selection component 254, and communication component 256. While these components are included in the embodiment of FIG. 2, any number of components, either more or less than the illustrated components, may be used to accomplish the purposes of the present invention. Other components and subcomponents are contemplated to be within the scope of the present invention. Furthermore, although depicted as residing on one device, such as a server, it will be appreciated that any number of components and/or subcomponents may reside on any number of computing devices or servers. For example, one or more components of line confirmation component 240 may reside on medical devices 212, 214 and/or clinical user device 226.

Indication component 252 is generally configured to provide an indication that one or more infusions need a line check. In this regard, the indication component may provide a list of infusions that have not received verification from the clinician that a line check has been performed. The indication component 252 may provide the list of infusions to the clinician via a user interface on a clinical user device 226.

Selection component 254 is generally configured to receive a selection of one of the one or more infusions. A specific infusion order is selected by the clinician and the system may highlight that infusion order. The selection is made by the clinician via the user interface provided on the clinical user device 226.

Communication component 256 is generally configured to establish communication between an EMR 229 associated with the patient and a medical device 210, 212, 214. In some embodiments, communication component 236 facilitates establishing communication between the EMR 229 and a medical device 210, 212, 214. In other embodiments, communication component 236 confirms that communication has been established between the EMR 229 and medical device 210, 212, 214. For example, communication component 226 may receive a confirmation from medical device 210, 212, 214, the EMR 229, or another component of system 200 indicating that communication has been established. Although communication is described as being between medical device 210, 212, 214 and the EMR 229, communication may be established between medical device 210, 212, 214 and another component of system 200. Communication may be made between medical device 210, 212, 214 and a component of system 200 directly, such as via bus 216, or as facilitated by some other component of system 200 not shown in FIG. 2 (such as via some other network or component in the cloud).

Once communication has been established, communication component communicates information corresponding to the selection of the one of the one or more infusions to a corresponding infusion pump. This causes the infusion pump to provide a visual indication of the line check and enables the clinician to efficiently confirm the appropriate infusion. As can be appreciated, when a patient is receiving several infusions, it may be difficult to identify the correct line for line confirmation. The visual indication of the line check helps prevent errors and increases efficiency in the clinician's workflow. Once the clinician has verified the line (e.g. right pump, right order, and right site), the visual indication for that pump may be turned off and the clinician may select a different infusion via the selection component 254.

Figure 3:
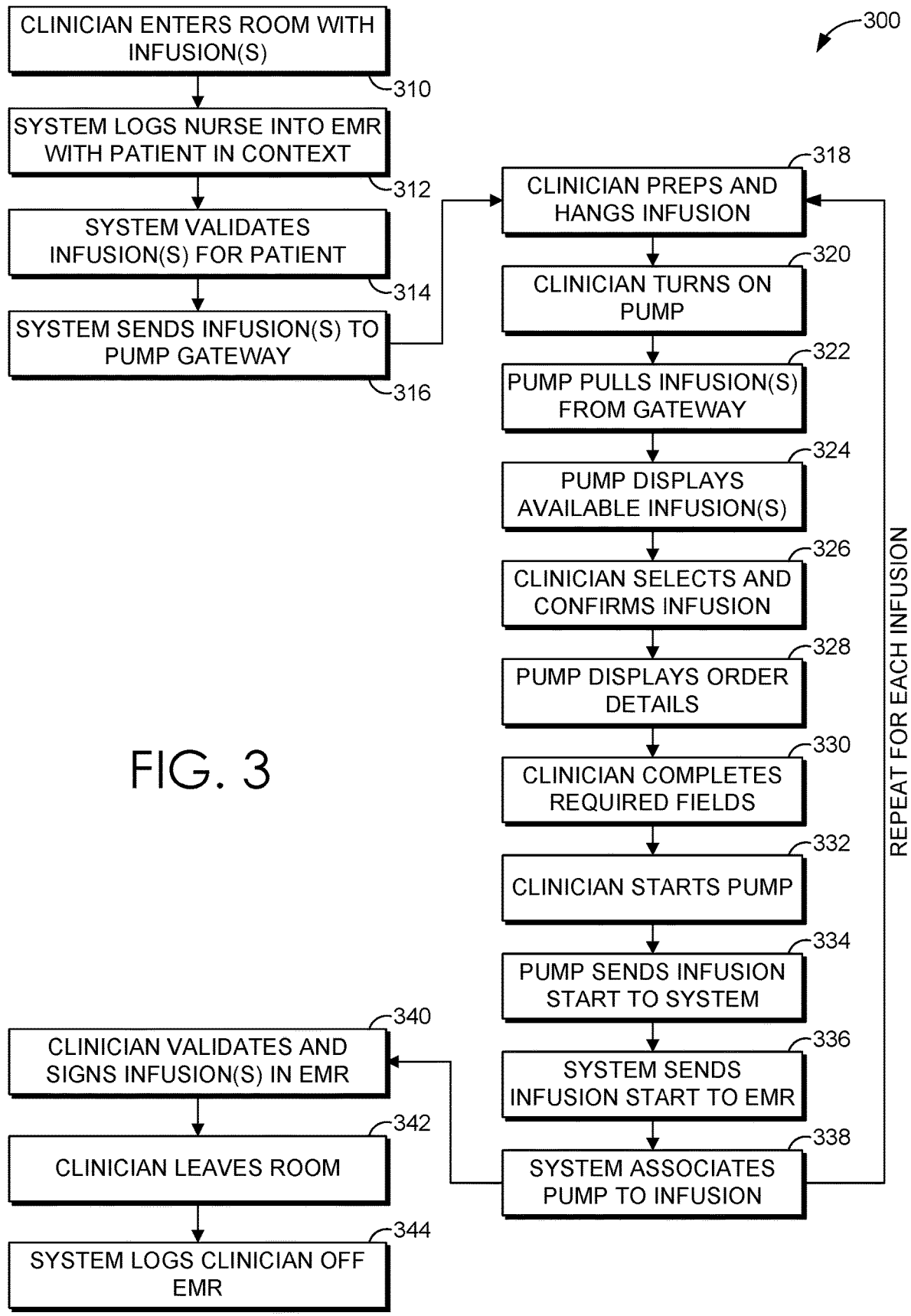
FIG. 3 is a flow diagram showing a method for providing infusion pump smart programming in accordance with embodiments of the present invention.

Turning now to FIG. 3, a flow diagram is provided that illustrates a method 300 for providing infusion pump smart programming, in accordance with embodiments of the present invention. Initially, at step 310, a clinician enters a room with one or more infusions. The system automatically logs the clinician into the EMR with patient information in context. For example, the patient and the infusion pump(s) are already in the room and the patient has already been associated to the infusion pump(s), such as by RFID association. Location tracking systems and/or proximity detection systems may also be utilized to associate the patient and the infusion pump(s). Accordingly, the system may log the clinician into the EMR and provide a list of one or more infusion orders for that patient.

At step 312, the system validates the one or more infusions for the patient. Any infusions that are incorrect will result in an alert on all devices and/or pumps (when turned on) and the clinician workflow will halt. Once the infusion (s) have been validated for the patient, at step 314, the system send infusion(s) to the pump gateway, at step 316. The infusion(s) may be initially communicated by the EMR directly (i.e., such as via bus 216 of FIG. 2) to the pump gateway or as facilitated by some other component not shown in FIG. 2 (e.g., such as via some other network or component in the cloud).

The clinician may began preparing and hanging the infusion, at step 318. Once the clinician turns on the pump, at step 320, the infusion(s) are pulled from the gateway to the pump(s), at step 322. At this point, each pump will display all available infusions, at step 324. The clinician selects and confirms the appropriate infusion for each particular pump, at step 326. At step 328, the pump displays the order details. If any fields are missing or require information, the clinician completes these fields at step 330.

The clinician starts the pump(s) at step 332. This causes the pump(s) to send an infusion start message to the system at step 334. The system sends the infusion start message to the EMR, at step 336, so the EMR can begin documenting data associated with the pump(s). Additionally, the system associates the pump to the infusion, at step 338. The clinician can then validate and sign the infusion(s) in the EMR, at step 340. Once the clinician leaves the room, at step 342, the system logs the clinician off the EMR, at step 344.

Figure 4:
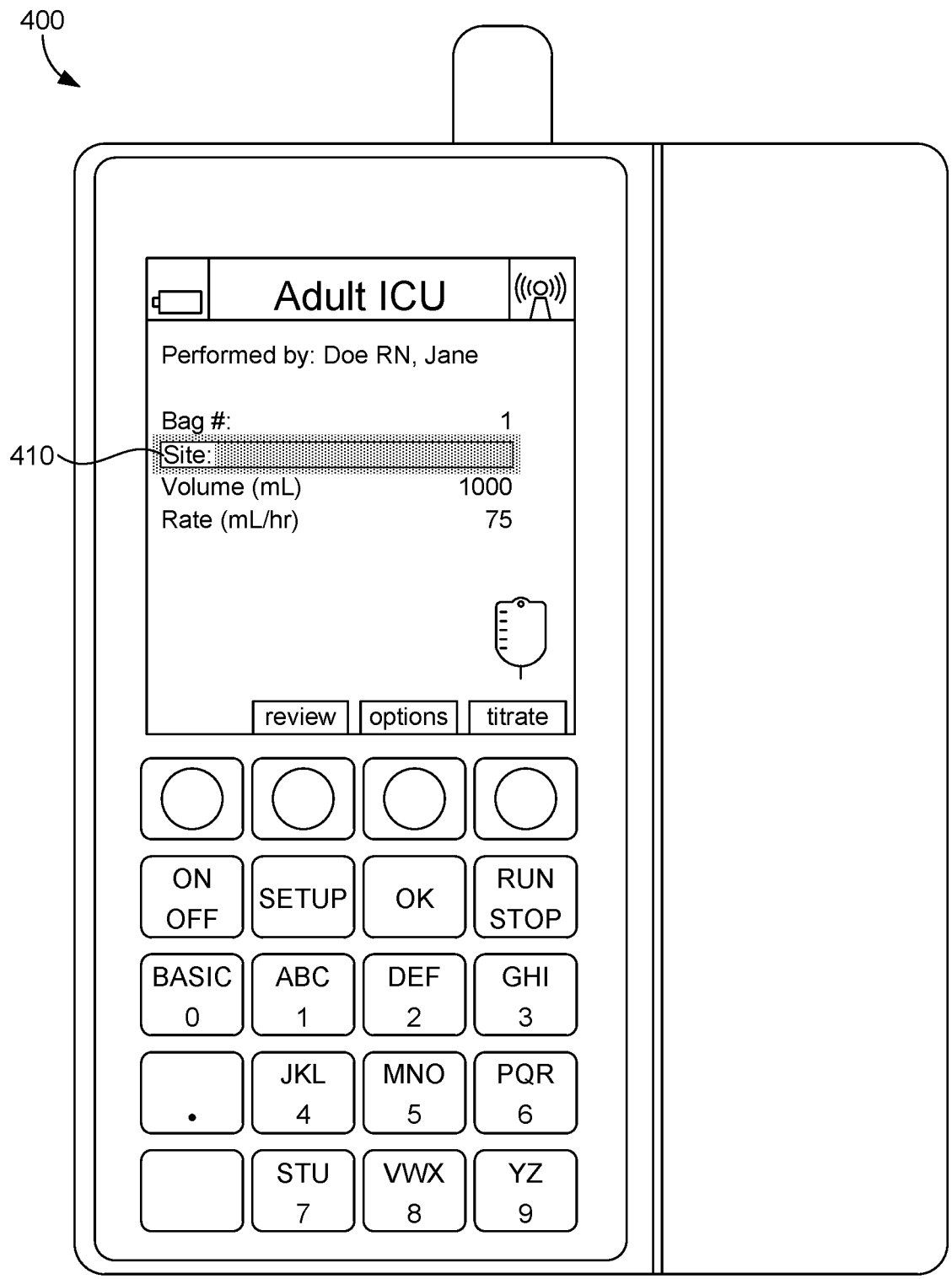
FIG. 4 is a screenshot of an exemplary graphical user interface in accordance with embodiments of the present invention.

FIG. 4 is an illustrative graphical user interface 400 providing infusion pump smart programming in accordance with embodiments of the present invention. As illustrated, user interface 400 provides a clinician with an infusion that has been pulled from the gateway to the pump. The infusion may have initially been selected by the clinician from a list of possible infusions. The order details for the selected infusion are displayed by the pump. Any missing fields for the selected infusion are highlighted, such as the site field 410 in this example. Once the clinician completes the missing field information, the clinician can start the pump. This will send the infusion start message to the system, which relays the message to the EMR so the EMR can begin documenting data associated with the pump.

Figure 5:
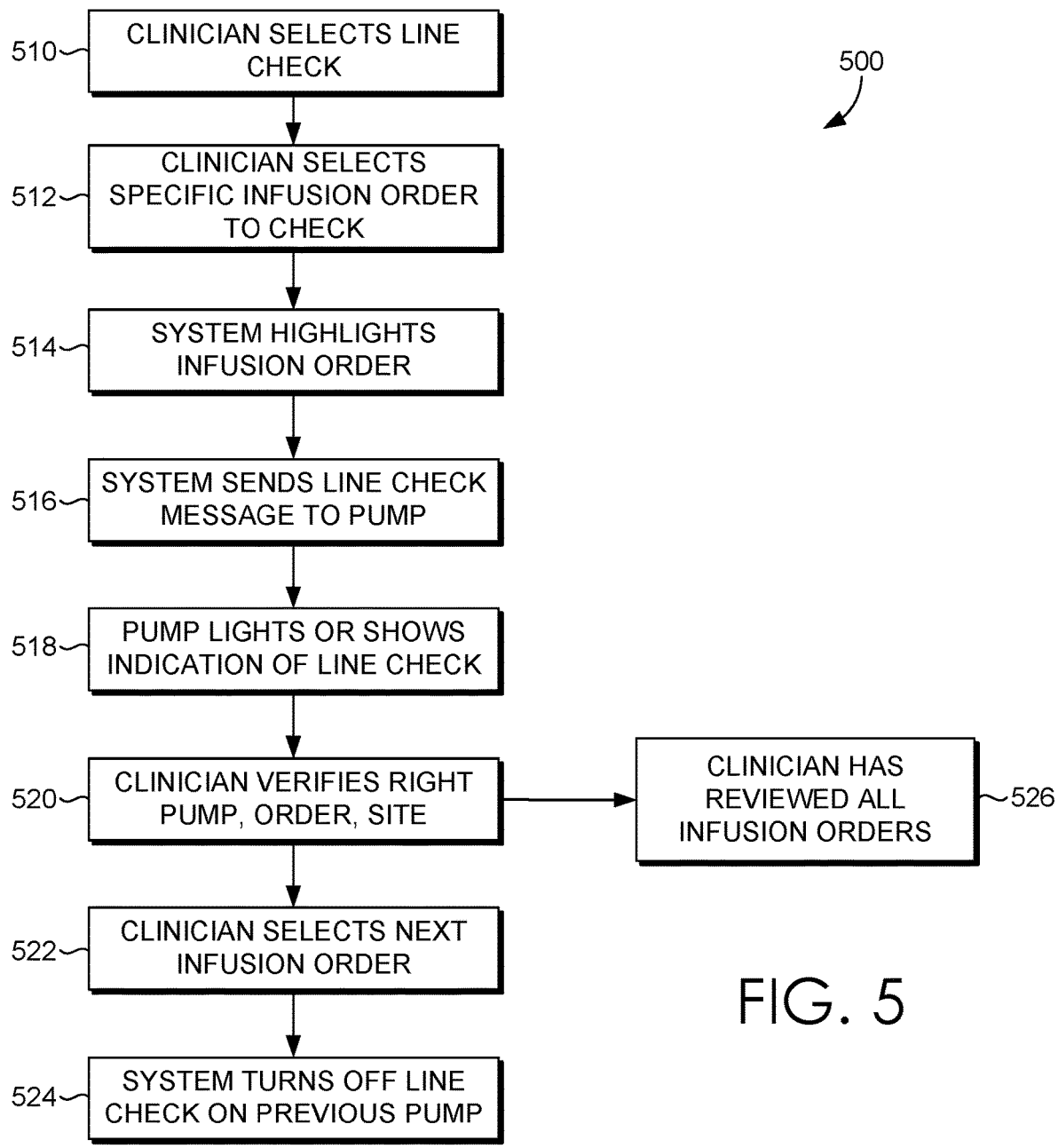
FIG. 5 is a flow diagram showing a method for providing infusion pump line confirmation in accordance with embodiments of the present invention.

With reference now to FIG. 5 a flow diagram is provided that illustrates a method 500 for providing infusion pump line confirmation, in accordance with embodiments of the present invention. Initially, at step 510, a clinician selects line check from the interface in the EMR. The clinician may additionally select a specific infusion order to check, at step 512. Once the clinician has selected a specific infusion order, the system highlights the infusion order, at step 514.

At step 516, the system sends a line check message to the pump. In some embodiments, the message is initiated at the EMR and communicated, such as via bus 216 of FIG. 2 or as facilitated by some other component not shown in FIG. 2 (e.g., such as via some other network or component in the cloud, to the pump gateway and ultimately, to the pump. Lights are displayed on the infusion pump, at step 518, as an indication of the line check. In some embodiments, other visual and/or audio indications of a line check may be provided by the pump.

Once the clinician has verified the right pump, order, and site, at step 520, the clinician may select the next infusion order, at step 522. This causes the system to turn off the line check on the previous pump, at step 524, and the process repeats from step 516. If the clinician has reviewed each infusion order, the process is terminated at step 526.

Figure 6:
FIG. 6 is a screenshot of an exemplary graphical user interface in accordance with embodiments of the present invention.

Referring to FIG. 6, an illustrative graphical user interface 600 is shown providing infusion pump line confirmation, in accordance with embodiments of the present invention. In FIG. 6, once the clinician has selected line check 610 from the EMR, available infusions are listed. Upon selecting an infusion 620 from the list, the selected infusion is highlighted. The selection also causes the process described above to begin.

Figure 7:
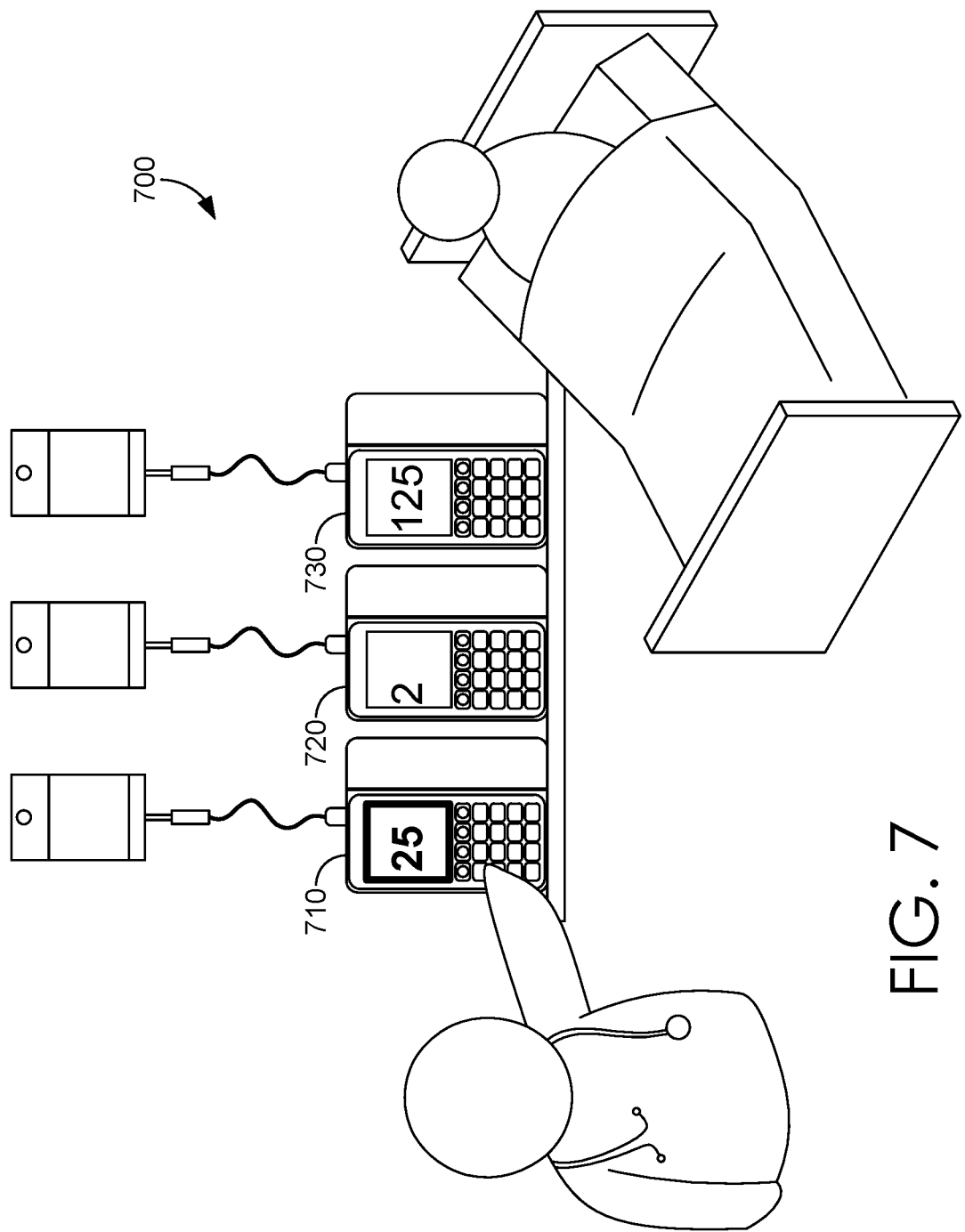
FIG. 7 is an illustration of an exemplary clinical setting 700 in accordance with embodiments of the present invention.

Referring now to FIG. 7, an illustration of an exemplary clinical setting 700 is shown, in accordance with embodiments of the present invention. After the infusion has been selected from the list, the system sends a line check message 710 to the pump. In some embodiments, the message is initiated at the EMR and communicated, such as via bus 216 of FIG. 2 or as facilitated by some other component not shown in FIG. 2 (e.g., such as via some other network or component in the cloud, to the pump gateway and ultimately, to the pump. In some embodiments, lights may be displayed as an indication of the line check to distinguish from other pumps 720, 730 in the room. In some embodiments, other visual and/or audio indications of a line check may be provided by the pump. After the clinician has verified the right pump, order, and site, the system turns off the line check on the pump 710.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

What is claimed is:

1. One or more non-transitory computer storage media storing computer-useable instructions that, when used by one or more computing devices, cause the one or more computing devices to perform operations comprising:
    providing, via a user interface on a clinician device, one or more infusions that need a line check validation between at least a patient and an infusion pump;
    receiving a selection, via an interaction with the user interface on the clinician device, of one of the one or more infusions corresponding to the infusion pump;
    providing, via the user interface on the clinician device, an indication of the selection;
    detecting, via a first sensor, that the clinician device is within a first proximity of the infusion pump;
    upon detecting that the clinician device is within the first proximity of the infusion pump, automatically performing the line check validation to the one of the one or more infusions that was selected, wherein the line check validation is performed without requiring barcode scanning and comprises:
        establishing a connection between the clinician device and an electronic patient-wearable device; and
        automatically validating the one of the one or more infusions selected and the infusion pump for the patient based on (1) the connection between the clinician device and the electronic patient-wearable device and (2) the clinician device being within the first proximity of the infusion pump; and
    displaying the line check validation via the user interface on the clinician device.

2. The media of claim 1, further comprising causing the infusion pump to provide a visual indication of the line check validation.

3. The media of claim 1, further comprising:
automatically providing, via the user interface on the clinician device, the one or more infusions that need the line check validation upon detecting that the clinician device has entered a particular room; and
upon displaying the line check validation via the user interface, receiving, via an interaction with the user interface on the clinician device, a second selection.

4. The media of claim 2, further comprising:
causing a visual indication of the infusion pump to turn off upon completion of the line check validation.

5. The media of claim 1, wherein the line check validation further includes verifying an association among the electronic patient-wearable device and the infusion pump, an order, and a site, the validation occurring wirelessly and without requiring barcode scanning, and wherein the media further comprises communicating the association to an electronic medical record for facilitating the one of the one or more infusions via the infusion pump to the patient.

6. The media of claim 1, further comprising communicating information corresponding to the selection of the one of the one or more infusions to a corresponding infusion pump.

7. The media of claim 1, further comprising documenting an infusion to an electronic medical record (EMR) upon automatically performing the line check validation.

8. The media of claim 7, further comprising communicating updates made by a clinician to a documentation corresponding to the infusion pump to the EMR.

9. A method for a line check, the method comprising:
receiving a selection, via an interaction with a user interface on a clinician device, of one of one or more infusions that need a line check validation;
providing, via an interaction with the user interface on the clinician device, an indication of the selection; and
automatically performing the line check validation to an infusion pump corresponding to the one of the one or more infusions upon detection that the clinician device is within a proximity of the infusion pump, wherein the line check validation is performed without requiring barcode scanning and comprises:
 detecting, via a sensor, that an electronic patient-wearable device is within a second proximity of the clinician device; and
 automatically validating the one of the one or more infusions selected and the infusion pump for a patient associated with the electronic patient-wearable device based on (1) detecting that the electronic patient-wearable device is within the second proximity of the clinician device and (2) detecting that the clinician device is within the proximity of the infusion pump; and
upon performing the line check validation, providing a notification to the clinician device.

10. The method of claim 9, further comprising:
upon completion of the one of the one or more infusions, causing the infusion pump to turn off;
receiving an additional selection, via an interaction with the user interface on the clinician device, of another of the one of the one or more infusions; and
automatically performing an additional line check validation upon detection that the clinician device is within a third proximity of a second infusion pump corresponding to the additional selection.

11. The method of claim 9, further comprising providing a visual indication and an audio indication of the line check validation in addition to the notification.

12. The method of claim 9, wherein, upon performing the line check validation, communicating the line check validation by a bus to the infusion pump, and wherein the method further comprises documenting, via an electronic medical record data associated with an infusion via the infusion pump.

13. The method of claim 9, further comprising providing, via the user interface on the clinician device, a list of infusions that have not yet received the line check validation.

14. A computer system useful for a line check validation, the system comprising:
a non-transitory memory device for storing computer readable program code; and
a processor in communication with the memory device, the processor being operative with the computer readable program code to:
 provide a list of infusions;
 provide an indication that one or more infusions in the list need the line check validation;
 select one of the one or more infusions in the list that need the line check validation;
 provide an indication of the selection; and
 automatically perform the line check validation to an infusion pump in response to the selection, wherein the line check validation is performed without requiring barcode scanning and comprises:
  detect that a clinician device is within a first proximity of an electronic patient-wearable device and that the clinician device is also within a second proximity of the infusion pump; and
  automatically validate the one of the one or more infusions selected and the infusion pump for a patient associated with the electronic patient-wearable device based on the first proximity and the second proximity; and
 provide a communication of the validation to an electronic medical record (EMR).

15. The system of claim 14, further comprising:
determine that an association between the electronic patient-wearable device and the infusion pump corresponds to a particular order.

16. The system of claim 14, further comprising:
automatically log a clinician into the EMR upon a detection that the clinician associated with the clinician device has entered a room in which the infusion pump is located.

17. The system of claim 15, further comprising:
receive information from a pharmacy application and determine that the information corresponds to the particular order.

18. The system of claim 17, further comprising transmit the information from the pharmacy application to the clinician device and another medical device via a bus.

19. The media of claim 5, further comprising facilitating the one of the one or more infusions via the infusion pump to the patient and documenting data corresponding to the facilitating to an electronic medical record.

* * * * *

UNITED STATES PATENT AND TRADEMARK OFFICE
CERTIFICATE OF CORRECTION

PATENT NO. : 11,295,845 B2
APPLICATION NO. : 14/965461
DATED : April 5, 2022
INVENTOR(S) : Kelly et al.

Page 1 of 1

It is certified that error appears in the above-identified patent and that said Letters Patent is hereby corrected as shown below:

In the Claims

Claim 12, Column 14, Line 8:
The line reading "record data associated with an infusion via the infusion" should read -- record, data associated with an infusion via the infusion --.

Signed and Sealed this
Sixteenth Day of August, 2022

Katherine Kelly Vidal
*Director of the United States Patent and Trademark Office*